US005938441A

United States Patent [19]

Brenner

[11] Patent Number: 5,938,441

[45] Date of Patent: Aug. 17, 1999

[54] AIR DRIVEN LOW SPEED DENTAL HANDPIECE MOTORS

[75] Inventor: Tod H. Brenner, Lancaster, Pa.

[73] Assignee: Den-Tal-Ez, Inc., Audubon, Pa.

[21] Appl. No.: 09/033,776

[22] Filed: Mar. 3, 1998

Related U.S. Application Data

[62] Division of application No. 08/724,137, Sep. 30, 1996, Pat. No. 5,795,167.

[51] Int. Cl.$^6$ .................................................. A61C 1/02

[52] U.S. Cl. ........................................ 433/132; 433/120

[58] Field of Search .................................. 433/100, 114, 433/120, 131, 132; 415/904

[56] References Cited

U.S. PATENT DOCUMENTS

| | | | |
|---|---|---|---|
| 3,942,392 | 3/1976 | Page, Jr. et al. | 433/132 |
| 4,040,311 | 8/1977 | Page, Jr. et al. | 415/503 |
| 4,278,427 | 7/1981 | Lingenhöle et al. | 433/100 |
| 4,403,958 | 9/1983 | Löhn | 433/100 |
| 4,504,227 | 3/1985 | Löhn | 433/132 |
| 4,642,051 | 2/1987 | Löhn | 433/100 |
| 5,096,418 | 3/1992 | Coss . | |
| 5,286,194 | 2/1994 | Horiuchi et al. | 433/132 |
| 5,476,380 | 12/1995 | Rosenstatter | 433/100 |
| 5,525,097 | 6/1996 | Kakimoto | 415/904 |

FOREIGN PATENT DOCUMENTS

| | | | |
|---|---|---|---|
| 1501579 | 11/1967 | France | 433/131 |
| 1 538 901 | 1/1979 | United Kingdom . | |
| 2047348 | 11/1980 | United Kingdom | 433/132 |
| WO 93/05723 | 4/1993 | WIPO . | |

OTHER PUBLICATIONS

Arron D. Deutchman, et al. *Machine Design Theory and Practice*, Macmillan Publishing Co., Inc. New York, NY, 1975, pp: Cover, Author, Copyright and 512 and 515.

Photocopy (1 page) of Micro Motors, Inc. "Titan II–Plus" Air Driven, Low Speed, Dental Handpiece Motor Valve Face and Guide Plate.

*Primary Examiner*—Ralph A. Lewis
*Attorney, Agent, or Firm*—Panitch Schwarze Jacobs & Nadel, P.C.

[57] ABSTRACT

Air driven dental handpiece motors include a tubular housing and a rotor rotatably supported within the housing. One motor is geared down by the provision of a plurality of idler gears rotatably supported on a hub which rotates between a sun gear on the output end of the rotor and a ring gear fixed within the housing. A drive shaft connects an exposed drive gear with the hub. A bearing is provided between the drive shaft and the inner bore of skirt extending from the ring gear to reduce a number of tolerances built up between the drive shaft and the bearing. The motor further includes a valve member rotatable through about 140° of arc to vary maximum motor speed and motor rotation direction. The valve member abuts a valve plate having a circular air inlet opening and a semicircular air outlet or exhaust opening. The valve member has an air supply opening which is an elongated arcuate slot having radiused circumferential ends. Shallow, curvilinear recesses are provided in line with circumferential outer and inner walls of the central slot at each circumferential end of the slot and provide fine, low speed adjustment capability to the valve. Deeper recesses at the center of the slot provide an effective air supply orifice diameter at least as great as the effective orifice diameter of the valve plate inlet air opening to maximize top motor speed.

4 Claims, 4 Drawing Sheets

AIR DRIVEN LOW SPEED DENTAL HANDPIECE MOTORS

CROSS REFERENCE TO RELATED APPLICATION

This application is a division of application Ser. No. 08/724,137, filed Sep. 30, 1996, now U.S. Pat. No. 5,795,167 entitled AIR DRIVEN LOW SPEED DENTAL HANDPIECE MOTORS, the entire disclosure of which is incorporated herein by reference.

FIELD OF THE INVENTION

The present invention relates to air driven dental equipment and, more particularly, to air driven, low speed dental handpiece motors.

BACKGROUND OF THE INVENTION

Air driven turbines have virtually supplanted all other types of dental handpiece drives. High speed air driven motors are typically located in a drive head which receives the burr or other tool. These motors reach speeds of hundreds of thousands revolutions per minute. However, because the heads need to be sterilized after each use, the operating lives of such heads are relatively short.

There remains a very significant market for so-called “low speed” motors. Such motors are generally located in the grip portion of the handpiece and are connected to the burr in a drive head spaced from the motor through a train of gears and shafts. Such low speed motors can achieve maximum burr speeds on the order of about 20,000 to 40,000 rpm depending upon manufacturer. The speed of such motors typically can be varied by varying the air supplied to the motor typically through a separate foot pedal control coupled with the air supply. However, it is very difficult to vary speed with such foot controls.

In addition, some air driven motors may be provided with speed control valves which limit maximum speed of the motors and even permit reverse rotation of such motors. Due to the miniature size of such motors and the use of air, high precision parts must be used. Alignment of these parts is important to assure smooth operation, long life and minimum air leakage for high efficiency. Moreover, due to their small size and air drives, resolution of the maximum speed of such motors is difficult to achieve. The valving provided to vary air flow must be sufficiently small to fit into the handpiece with the rotor to provide a self-contained unit.

SUMMARY OF THE INVENTION

In one aspect the invention is an air driven dental handpiece motor comprising a tubular outer housing sufficiently small in diameter to enable the housing to be gripped in one hand using only fingers of the hand; a rotor with a plurality of vanes rotatably supported in the housing; a sun gear coupled with one axial end of the rotor; a plurality of idler gears; a hub rotatably supporting the plurality of idler gears in engagement with the sun gear; a drive shaft coupled with the hub and axially aligned with the rotor, the drive shaft projecting axially away from the rotor; a drive gear coupled with an end of the drive shaft distal to the hub; a ring gear engaged with the plurality of idler gears, the ring gear surrounding the sun gear and the plurality of idler gears, the ring gear including a skirt defining central bore extending axially away from the idler gears, the bore receiving the hub and a portion of the drive shaft; and a bearing located between the drive shaft and the central bore of the ring gear skirt centering the drive shaft with respect to the ring gear during rotation of the drive shaft.

In another aspect the invention is an adjustable air driven dental handpiece motor comprising: a tubular housing; a rotor with a plurality of vanes supported for rotation within a chamber within the housing; a valve member within the housing; a valve plate within the housing between the valve member and the chamber, a first air passageway extending through the valve plate to the chamber and a second air passageway separate from the first air passageway extending from the chamber through the valve plate to the valve member; and the valve member having an end face contacting the valve plate, an air supply opening through the valve member and the end face and an air exhaust opening spaced from the air supply opening at the valve member end face, the air supply opening includes a central slot defined by two circumferentially extending, concentrically located outer and inner walls connected by radius walls at their circumferential ends, and at least two, generally semicircular recesses in the valve member end face, one recess at each circumferential end of the central slot, at least one of the valve member and the valve plate being rotatable within the housing.

In yet another aspect the invention is an adjustable air driven dental handpiece motor comprising: a tubular housing; a rotor with a plurality of vanes supported for rotation within a chamber within the housing; a valve member within the housing; a valve plate within the housing between the valve member and the chamber, a first air passageway extending through the valve plate to the chamber and a second air passageway separate from the first air passageway extending from the chamber through the valve plate to the valve member; and the valve member having an end face contacting the valve plate, an air supply opening through the valve member and the end face and an air exhaust opening spaced from the air supply opening at the valve member end face, the air supply opening includes a central slot defined by two circumferentially extending, concentrically located outer and inner walls connected by radius walls at their circumferential ends, and an outer recess in the end face extending from a central portion of the central slot towards a circumferential outer perimeter of the end face, the outer recess and the central slot defining a pair of circumferential walls of the end face on either side of the outer recess, the circumferential walls extending along an outer peripheral portion of the valve end face, and at least one of the valve member and the valve plate being rotatable within the housing.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF PREFERRED EMBODIMENTS

Figures 1, 2, 3:
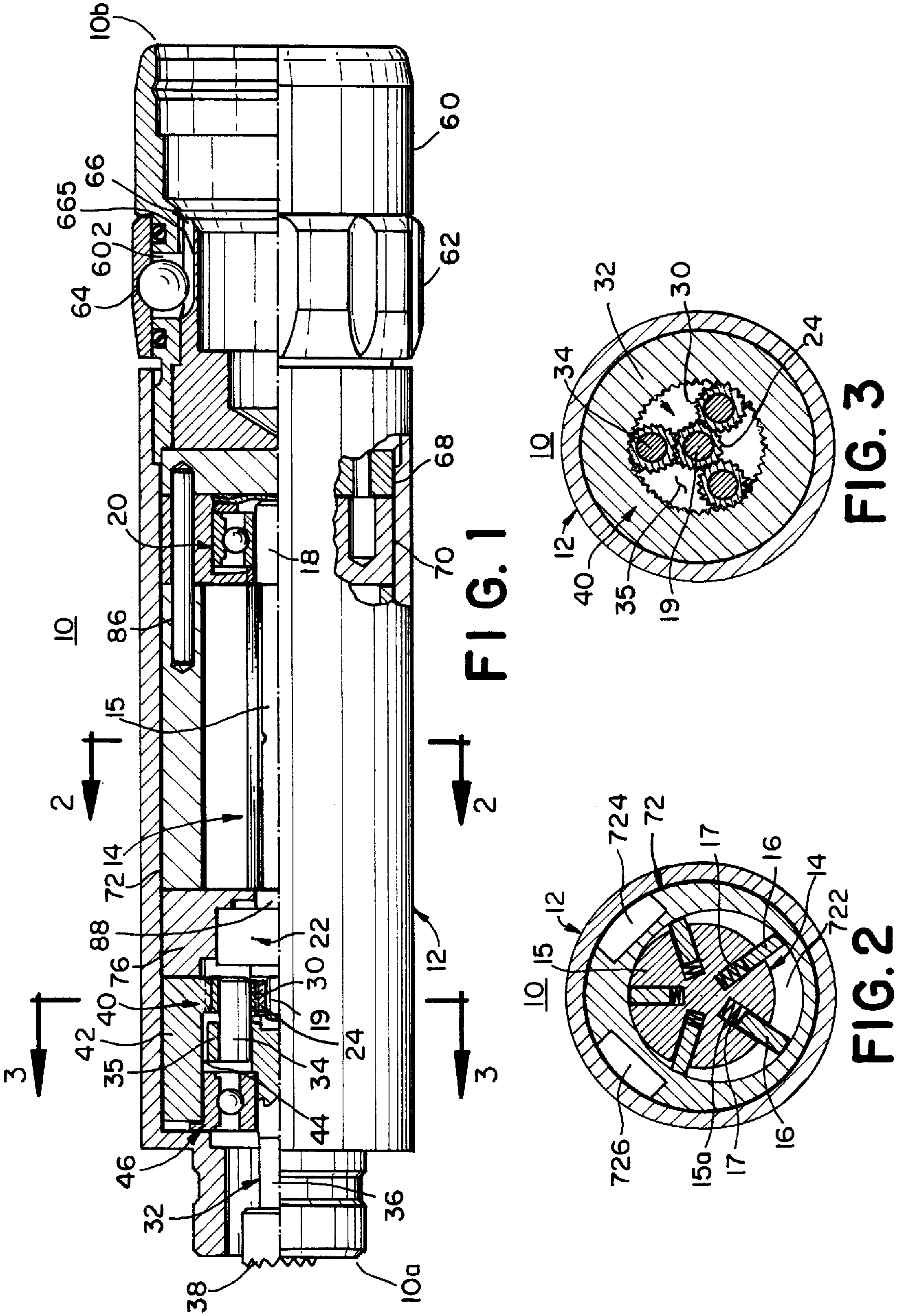
FIG. 1 is a quarter sectioned and partially broken away side elevational view of an air driven dental handpiece motor of the present invention.
FIG. 2 is a cross section taken along the lines 2—2 of FIG. 1.
FIG. 3 is a cross section taken along lines 3—3 of FIG. 1.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the and designated parts thereof. The words "front" and "rear" refer to the opposing burr drive end and air supply end of the motor. The terminology includes the words above specifically mentioned, derivatives thereof and words of similar import.

Referring to the drawings, like numerals indicate like elements throughout. A preferred embodiment air driven dental handpiece motor, indicated generally at 10 is shown in FIG. 1. A front end 10*a* of the motor 10 is configurated (i.e. sized and shaped) to mate with and, preferably, releasably engage a drive head (not depicted) holding the burr or other tool. The rear end 10*b* of the motor 10 is configured to mate with and, preferably, releasably engage a dental handpiece air supply coupling (not depicted) either swivel or fixed back end type couplings. The overall construction of such motors, couplings and handpieces is well-known in the industry.

Motor 10 includes a generally tubular outer housing 12, sufficiently small in diameter to enable the housing 12 to be gripped and manipulated in only one hand by an operator using only fingers of the hand like a pen or other writing instrument. An air driven rotor indicated generally at 14 is rotatably supported in the housing 12 on bearings 20, 22. Referring to FIG. 2, rotor 14 is preferably an assembly including a central hub 15 receiving a plurality of vanes 16 in radial slots 15*a* extending the length of the hub 15 and biased outwardly by springs 17. Referring back to FIG. 1, a pair of stub shafts 18, 19 integral with the hub 15 extend from opposite axial ends of the hub 15 and are received in the bearings 20, 22, respectively. A sun gear 24 is fixedly coupled to one axial end of rotor 14 at the free, distal end of the rotor shaft 19, projecting through the bearing 22. Referring to FIGS. 1 and 3, an idler gear carrier indicated generally at 32 rotatably supports a plurality of idler gears 30, suggestedly three in number. Carrier 32 includes a hub 35 fixedly supporting shafts 34, which rotatably support the idler gears 30 in engagement with the sun gear 24. Carrier 32 further includes a drive shaft 36, which is fixedly coupled to hub 35 axially aligned with the rotor shafts 18, 19 and which project axially away from rotor 14. A crown-type drive gear 38 is fixedly coupled with an end of a drive shaft 36 distal to the hub 35. Drive gear 38 is exposed to view at the "forward" end 10*a* of the motor 10 within the open forward end of housing 12. Referring also to FIG. 3, a ring gear 40 is engaged with the idler gears 30 and surrounds the idler gears 30 and sun gear 24. The ring gear 40 further includes a cylindrical skirt portion 42 defining a cylindrical bore 44 extending axially away from idler gears 30. Skirt portion 42 and bore 44 receive and surround the hub 35 of the idler gear carrier 32 and a portion of the drive shaft 36. According to an important aspect of the invention, a bearing 46 is located between the drive shaft 36 of the idler gear carrier 34 and the ring gear 40 within the central bore 44. Bearing 46 centers the drive shaft 36 with respect to the ring gear 40 during rotation. This reduces by at least one the total number of tolerances built up between the drive shaft 36 and the bearing 46 and provides the proper gear mesh as evidenced by smooth start-up of the motor 10 at low inlet air pressures.

Motor 10 includes a number of other components at least one function of which is to control and direct pressurized air through the rotor 14. These are most conveniently identified from the rear end 10*b* of the motor where the air supply is introduced and exhausted. The rear end 10*b* of the motor is defined by an end cap 60. A speed adjustment ring 62 is rotatably mounted on the end cap 60 and retained between a step on the end cap 60 and the rear end of housing 12. The end cap 60 retains a speed adjustment valve 66 in motor 10. Valve 66 is coupled to ring 62 and end cap 60 by a ball 64, which travels along a transverse slot 602 that extends circumferentially partially around the end cap 60 through about 140° of arc. A valve plate 68 abuts a forward end of the speed adjustment valve 66. A forward end of the end cap 60 is located in an annular recess provided between the valve plate 68 and the inner bore of housing 12, fixing the valve plate 68 and end cap 60 with the housing 12. The end cap may be threaded to the housing 12 or press fit into the annular recess. A forward face of the valve plate 68 abuts a rear face of a rear end plate 70. A rear face of a cylinder 72 abuts the forward face of the rear end plate 70. A rear face of a forward end plate 76 abuts a forward face of the cylinder 72. End plates 70, 74 and a bore 722 of cylinder 72 define a chamber in which rotor 14 rotates. Referring to FIG. 3, the bore 722 is eccentrically located in cylinder 72 while rotor hub 15 is centrally located thereby creating a rotary vane motor with rotor 14. The planetary arrangement including idler gears 30, carrier 34 and ring gear 40 reduces the speed and increases the torque passed to drive gear 38. The depicted motor has a top forward speed of about 5000 RPM. The rotor, however, has a top speed of about 20,000 RPM. A 20,000 RPM motor is supplied simply by substituting drive gear 38 for sun gear 24 on the end of rotor shaft 19 and eliminating the rotary components of motor 10 forward of that gear.

Figure 4:
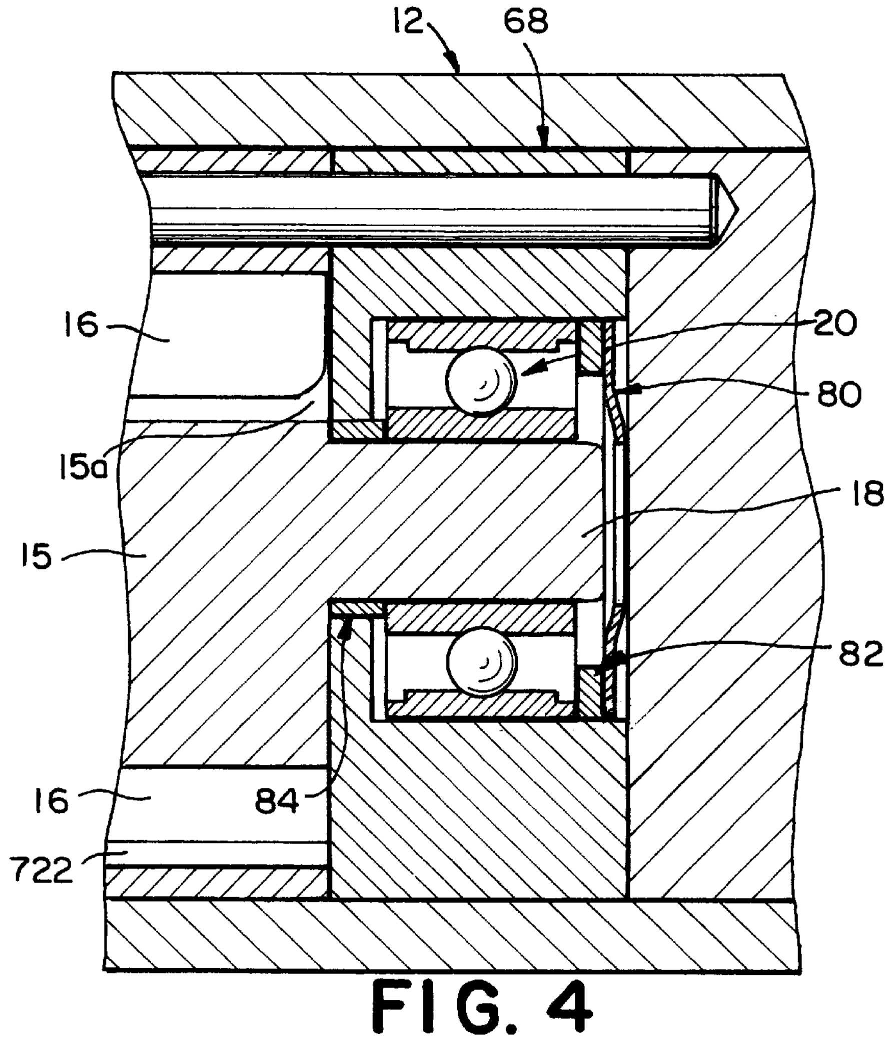
FIG. 4 is an expanded, cross-sectional view of the rear support of the rotor.
Figure 5:
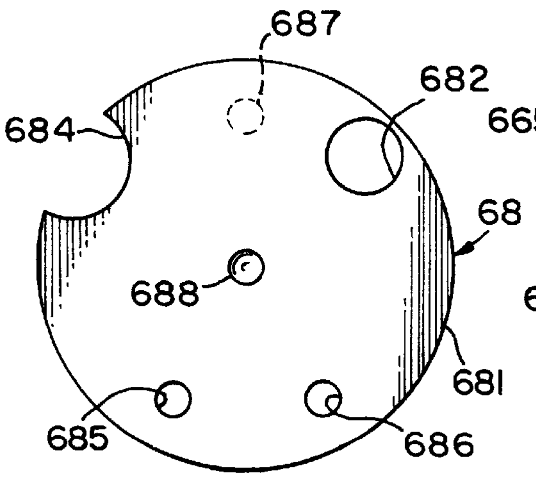
FIG. 5 is a rear elevation of the valve plate.

FIG. 4 depicts in expanded form, the components supporting the rear end of rotor 14. A spring or wave washer 80 and spacer 82 are located between valve plate 68 and bearing 20. Spacer 82 has a central opening sufficiently large so that the spacer 82 bears only on the outer race of bearing 20. Another spacer 84 on shaft 18 extends between the inner race of bearing 20 and the hub 15 of rotor 14 and is biased against hub 15 by spring washer 80, which also bears upon the inner race of bearing 20. Spring washer 80 takes up wear in the rotor support and enables a relatively light preload (e.g. about 24 ounces) to be maintained on bearing 20, 22 during the life of the motor 10. This promotes longer bearing life and provides smoother motor operation. Referring back to FIG. 1, an alignment pin 86 extends from cylinder 72 through rear end plate 70 and into the valve plate 68 and keeps those components aligned. Another spacer 88 is provided around stub shaft 19 at the forward end of rotor 14 between its hub 15 and the inner race of bearing 22. This arrangement is used in both 5,000 and 20,000 RPM versions of motor 10.

FIGS. 5–8 show the valve components primarily responsible for speed adjustment and reversal of the motor 10 in either 5,000 or 20,000 RPM versions. Valve plate 68 has a circular outer perimeter 681 and includes a circular air inlet opening 682 therethrough near the circular outer perimeter 681 of the valve 68 and a semicircular air outlet or exhaust opening 684 intersecting the outer perimeter 681 approximately 117° away from the inlet air opening 682. Valve stop pins 685 and 686 are located approximately 63° apart. A blind bore 687 receives the end of alignment pin 86. Lastly, central bore 688 is provided to assure that the adjustable valve member 66 seats fully against the valve plate 68 to form an air seal. The rear face of valve plate 68 depicted in FIG. 5 abuts the front face of adjustment valve member 66 depicted in FIG. 6.

Figure 6:
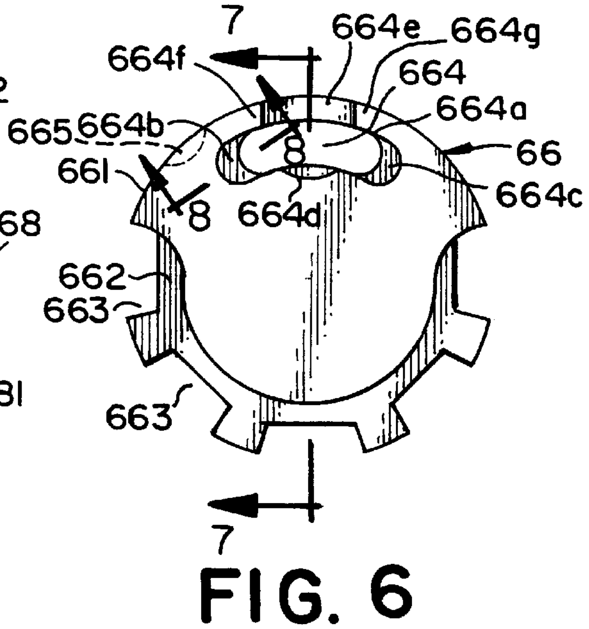
FIG. 6 is a front elevation of the speed adjustment valve.

Referring to FIG. 6, adjustable valve member 66 has a generally circular outer perimeter 661. Referring to FIGS, 6 and 7, a partially circumferential recess 662 extends approximately 210° around the lower circumferential portion of the depicted valve face and provides a circumferential channel connecting five uniformly sides generally a rectangularly-shaped slot 663 which extend along the circumferential outer surface of the valve member along the remainder of its length and provide air outlet channels. Ends of the recess also define stops for pins 685, 686. An air supply opening is indicated generally at 664, is provided along the upper circumferential portion of the valve member 66 and is symmetric with respect to the recess 662 and slots 663. Lastly, a slot 665 which extends part way along the length of the valve member 66 from its rear end and which receives ball 64 coupling valve member 66 with the speed adjustment ring 62 is indicated in phantom.

Figure 8:
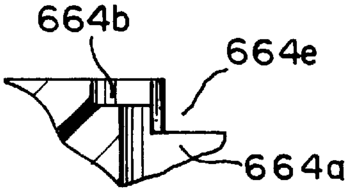
FIG. 8 is a cross section taken along the lines 8—8 of FIG. 6.

Referring to FIG. 6, the primary structure of the supply opening 664 is a central slot **664*a* which is elongated in circumferential direction and extends entirely through the face of the adjustable valve member 66. The central slot 664*a* has two circumferentially extending concentrically located outer and inner walls. The circumferentially extending walls are radiused at their circumferential ends. The radial width of central slot 664*a* is approximately 0.065". The air supply opening 664 further includes two shallow, generally semicircular recesses or lands 664*b*, 664*c* in line with the circumferential outer and inner walls of the central slot 664*a* at each circumferential end of the slot 664*a*. Centers of the semicircular recesses 664*b*, 664*c* are located just beyond the radiused circumferential ends of the central slot 664*a*. Referring to FIG. 8 where it is shown, the depth of the recess 664*b* is only approximately 0.020". Recess 664*c*** has the same depth.

Figure 7:
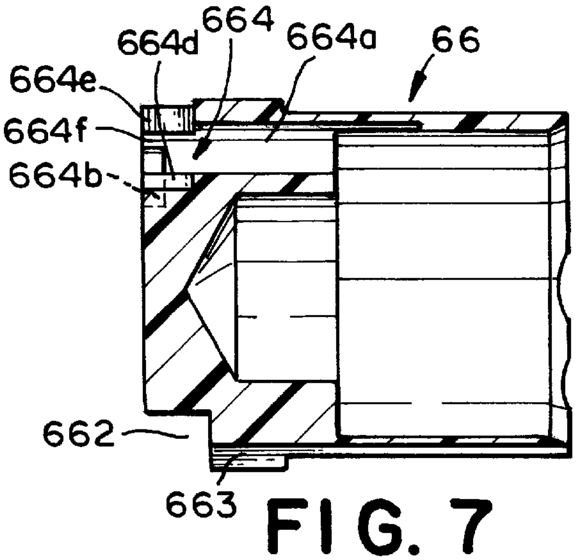
FIG. 7 is a cross section taken along the lines 7—7 of FIG. 6.

Referring back to FIGS. 6 and 7, deeper central recesses **664*d* and 664*e* are provided below (radially inwardly from) and above (radially outwardly from) the central slot 664*a*. The inner recess 664*d* is a portion of a semicircle approximately twice the width of the central slot 664*a* centered at the center of the slot 664*a*. The upper, outer recess 664*e* extends from the central slot 664*a* to the outer perimeter 661 of the valve member and has a width equal to the diameter defining recess 664*d*, which is approximately 25 percent greater than the diameter of the air inlet opening 682 of the valve plate 68. Referring to FIG. 7, the depths of recesses 664*d* and 664*e* is approximately 0.07" in the depicted embodiment. The overall valve radius is about 0.24". Central slot 664*a* and central recesses 664*d* and 664*e* define two circumferential walls or arms 664*f* and 664*g* on either side of outer recess 664 along the outer peripheral portion of the valve end face. Arms 664*f* and 664*g* seal flush against the rear face of valve plate 68**.

The recesses **664*b*–664*e* and walls 664*f*, 664*g* present a varying air supply opening geometry to the circular air inlet opening 682 of the valve plate 68 as the adjustable valve member 66 is rotated with respect to the valve plate 68 and air outlet opening 684. FIGS. 9–13 show various positions of the inlet and outlet openings 682, 684 of the valve plate 68 (in phantom) with respect to the air supply opening 664 and partial circumferential recess 662 leading to the exhaust slots 663 of the valve member 66**.

Figure 9:
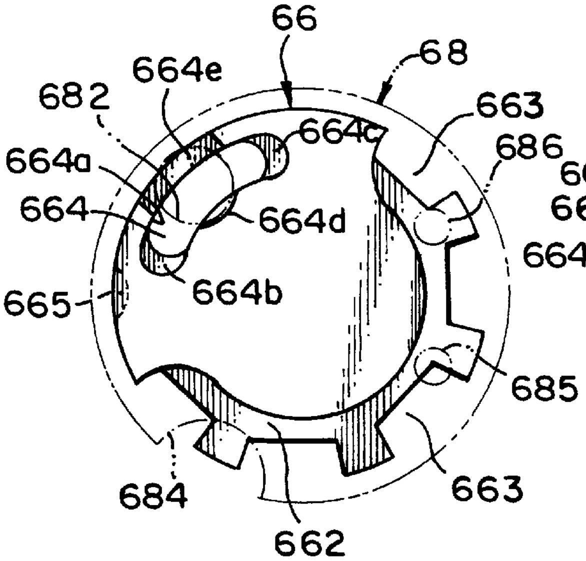
FIG. 9 depicts diagrammatically the control valve of the motor 10 in the full forward drive position.

In FIG. 9, the air inlet opening 682 of the valve plate 68 is centered over the air supply opening 664 of the adjustable valve member 66 providing full, direct and maximum air flow. The effective air supply orifice diameter presented to the circular inlet air opening 682 of valve plate 68 is preferably at least equal to or slightly greater than the effective orifice diameter of the circular inlet air opening 682.

Figure 10:
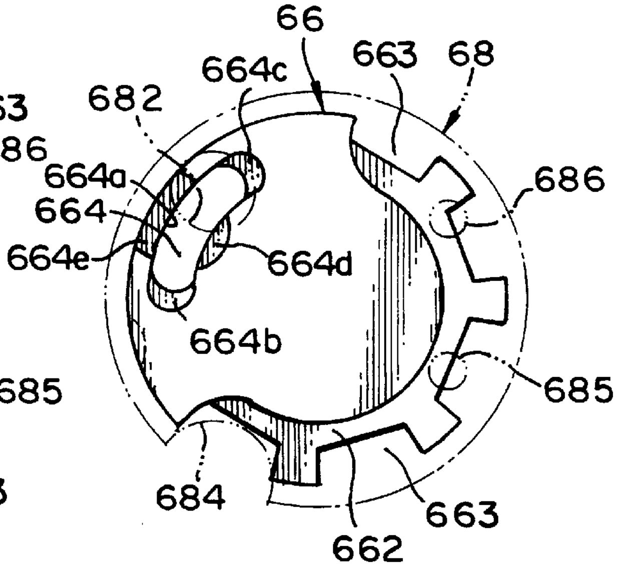
FIG. 10 depicts diagrammatically the control valve of the motor 10 in throttled forward drive position.

FIG. 10 depicts the adjustable valve member 66 in a partially throttled position. In reaching that position, the sharp edge of the radially outwardly located wall **664*f* adjoining the air inlet opening 664*a* almost immediately intersects and then partially covers the air inlet opening 682 in increasing degrees. Before the air inlet opening 682 passes completely from the outer recess 664*e*, a portion of the air inlet opening 682 has begun to pass over the shallow semicircular recess 664*c*. As the valve 66 continues to be rotated, the shallow semicircular recess 664*c* passes across and finally completely by the air inlet opening 682 until the position shown in FIG. 11** is reached.

Figure 11:
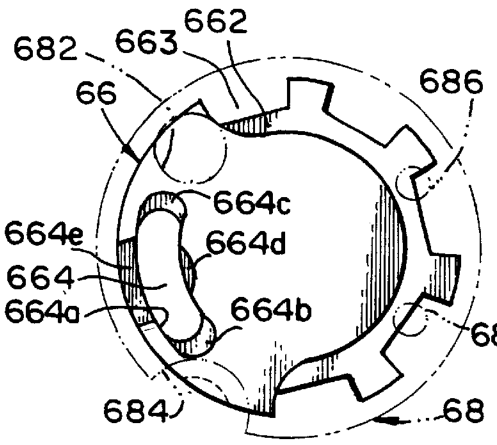
FIG. 11 depicts diagrammatically the control valve of the motor 10 in the closed or neutral position.

In FIG. 11, the forward end face of the adjustable valve member 66 fully covers and closes the air inlet opening 682 of the valve plate 68 while another portion of the adjustable valve member 66 forward end face covers the semicircular air outlet opening 684 of the valve plate 68. In this position, the motor 10 is considered to be in neutral and has insufficient air flow to turn the rotor 14.

Figure 12:
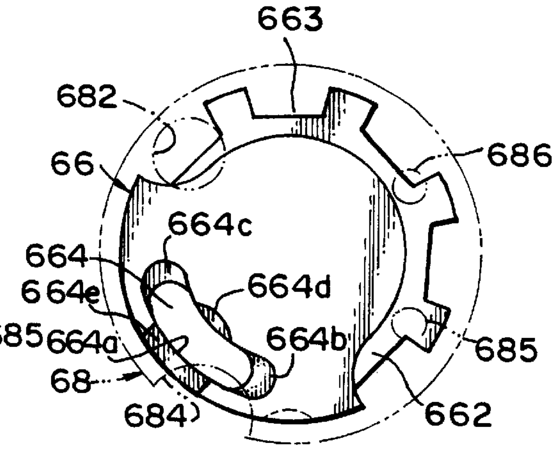
FIG. 12 depicts diagrammatically the control valve of the motor 10 in the throttled reverse position.
Figure 13:
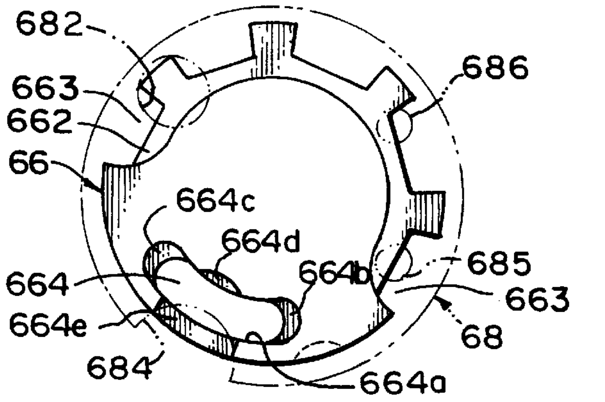
FIG. 13 depicts diagrammatically the control valve of the motor 10 in the full reverse drive position.

As the adjustable valve member 66 is rotated further in a counterclockwise direction as shown in FIGS. 12 and 13, the semicircular outlet air opening 684 of the valve plate 68 begins to overlap the shallow semicircular recess **664*b* of the air supply opening 664 while air inlet opening 682 of the valve plate 68 starts overlapping the partially circumferential recess 664 extending to the air exhaust channels or slots 663 along valve member 66. As a result, air begins to flow in a "reverse" direction through the valve plate 68 "inlet" and "outlet" openings 682 and 684 and through the remainder of the motor 10, thereby driving the rotor 14 in a reverse direction. FIG. 13 depicts the full open reverse orientation of the adjustable valve member 66 and valve plate 68 with the semicircular air outlet opening 684 of the valve plate 60 centered over the central slot 664*a* of air supply opening 664 and the deeper recesses 664*d* and 664*e* around that slot. Contact of stop pins with the ends of the partial circumferential recess 662 are shown in FIGS. 9 and 13, the full forward and reverse positions of valve member 68**.

By way of example, at full rpm, the supply pressure and exhaust pressure of air supply through the adjustable valve member might be approximately 43 psi and 10 psi, respectively to pass air at a rate of 0.85 cu. ft./min. through the motor 10 at full 20,000 rpm (unloaded). The effective orifice provided by the circular air inlet opening 682 of the valve plate 68 and the air supply opening 664 of the adjustable valve member 66 is selected to provide approximately half of the maximum air flow (e.g. 0.42 cu. ft./min.) when the adjustable valve 66 is positioned in the middle position between the full throttle and neutral positions of the valve. That effective orifice size was, for example, about 0.035 in. The deep central recesses 664*d* and 664*e* provide spaces where air passing through central slot 664*a* can be collected from ends of the slot and be presented directly to the valve plate inlet 682 over an area more uniformly surrounding the inlet 682. Arms 664*f* and 664*g* provide immediate, gross speed adjustments in the middle ranges. Shallow recesses 664*b* and 664*c* contribute to that adjustment. The shallow, semicircular recesses 664*b* and 664*c*, in particular, further provide fine adjustment at the low speed ranges formerly lacking in earlier designs of such motor, between the mid-speed position of valve member 66 and its neutral position.

Figure 14:
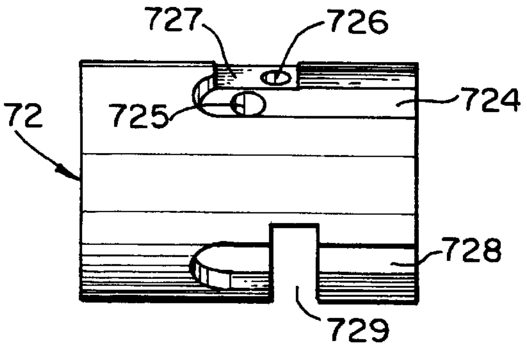
FIG. 14 is a top plan view of the motor cylinder.
Figure 15:
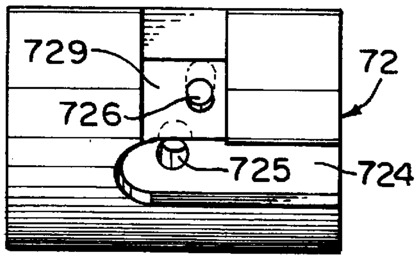
FIGS. 15 and 16 are side elevations of the motor cylinder viewed about 90° in either direction from FIG. 14 about a central axis.
Figure 16:
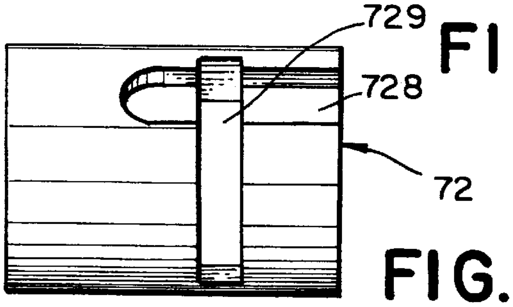

Completing the description of the air supply system within the motor 10, FIGS. 14 through 16 depict details of the flow channels along cylinder 72. These channels carry air between the valve plate 68 and the rotor chamber 722 (FIG. 2). Referring further to FIG. 14, which is a top plan view of the cylinder 72 as it would be positioned within the motor 10, blind-ended inlet and outlet channels 724, 728 are provided in the outer cylindrical surface of the cylinder extending from the rear end towards the forward end at roughly symmetric positions on either side of the center line of the cylinder 72. Referring to FIG. 15, a pair of jet hole 725, 726 are provided extendingly radially through the cylinder wall and into its hollow interior forming chamber 722 at angles selected to strike the vane surfaces and rotate the rotor 14 in a "forward" direction. Terminations of the holes are shown in phantom. Jet hole 726 is spaced circumferentially from jet hole 725 in a circumferentially extending recess 727 projecting from inlet channel 724 to space the jet holes 725, 726 sufficiently apart to enable them to simultaneously strike separate vanes with their jets. An exhaust slot 729 extends completely through the side wall of cylinder 72 and circumferentially about 135° around the outer circumference of the cylinder 72 to collect air from between a number of adjoining vanes at the same time. Slot 729 is a straight cut milled into the wall of cylinder 72 for ease of manufacture, but might take other shapes. It will be appreciated that because of the specialization of the channels 724 and 728 to optimize "forward" rotation of the rotor 14, motor 10 does not provide the same maximum speed and torque in a reverse direction as it does in the forward direction.

It will be appreciated by those skilled in the art that changes could be made to the embodiments described above without departing from the broad inventive concept thereof. For example, while the semicircular air supply opening recess geometries of the adjustable valve member are preferred, other non-circular but curvilinear recess and wall geometries might be used. It is understood, therefore, that this invention is not limited to the particular embodiments disclosed, but it is intended to cover modifications within the spirit and scope of the present invention as defined by the appended claims.

I claim:

1. An air driven dental handpiece motor comprising:

a tubular outer housing sufficiently small in diameter to enable the housing to be gripped in one hand using only fingers of the hand;

a rotor with a plurality of vanes rotatably supported in the housing;

a sun gear coupled with one axial end of the rotor;

a plurality of idler gears;

a hub rotatably supporting the plurality of idler gears in engagement with the sun gear;

a drive shaft coupled with the hub and axially aligned with the rotor, the drive shaft projecting axially away from the rotor;

a drive gear coupled with an end of the drive shaft distal to the hub;

a ring gear engaged with the plurality of idler gears, the ring gear surrounding the sun gear and the plurality of idler gears, the ring gear including a skirt defining a bore extending axially away from the idler gears, the bore receiving the hub and a portion of the drive shaft; and a bearing located between the drive shaft and the central bore of the ring gear skirt centering the drive shaft with respect to the ring gear during rotation of the drive shaft.

2. The motor of claim 1 wherein the drive gear is exposed to view at one axial end of the motor.

3. The motor of claim 2 wherein the one axial end of the motor is configured to releasably engage a dental handpiece burr drive head.

4. The motor of claim 2 wherein a remaining axial end opposite the one axial end is configured to releasably engage a dental handpiece air supply coupling.

* * * * *